(12) United States Patent
Warman

(10) Patent No.: US 6,317,626 B1
(45) Date of Patent: Nov. 13, 2001

(54) METHOD AND APPARATUS FOR MONITORING HEART RATE

(75) Inventor: Eduardo N. Warman, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/433,286

(22) Filed: Nov. 3, 1999

(51) Int. Cl.[7] ................................................ A61B 5/0432
(52) U.S. Cl. ............................................. 600/523; 607/59
(58) Field of Search ................................ 600/508, 509, 600/510, 522, 523; 607/5, 9, 32, 30, 59

(56) References Cited

U.S. PATENT DOCUMENTS

| | | |
|---|---|---|
| 4,223,678 | 9/1980 | Langer et al. . |
| 4,295,474 | 10/1981 | Fischell . |
| 4,374,382 | 2/1983 | Markowitz . |
| 4,428,378 | 1/1984 | Anderson et al. . |
| 4,535,774 | 8/1985 | Olson . |
| 4,625,730 | 12/1986 | Fountain et al. . |
| 5,107,833 | 4/1992 | Barsness . |
| 5,113,869 | 5/1992 | Nappholz et al. . |
| 5,117,824 | 6/1992 | Keimel et al. . |
| 5,135,004 | 8/1992 | Adams et al. . |
| 5,168,871 | 12/1992 | Grevious . |
| 5,176,137 | 1/1993 | Erickson et al. . |
| 5,179,947 | 1/1993 | Meyerson et al. . |
| 5,184,615 | 2/1993 | Nappholz et al. . |
| 5,251,626 | 10/1993 | Nickolls et al. . |
| 5,273,049 | 12/1993 | Steinhaus et al. . |
| 5,292,343 | 3/1994 | Blanchette et al. . |
| 5,312,446 | 5/1994 | Holschbach et al. . |
| 5,314,450 | 5/1994 | Thompson . |
| 5,324,315 | 6/1994 | Grevious . |
| 5,330,505 | 7/1994 | Cohen . |
| 5,331,966 | 7/1994 | Bennett et al. . |
| 5,354,319 | 10/1994 | Wyborny et al. . |
| 5,383,909 | 1/1995 | Keimel . |
| 5,431,685 | 7/1995 | Alt . |
| 5,489,293 | 2/1996 | Pless et al. . |
| 5,509,927 * | 4/1996 | Epstein et al. .......................... 607/32 |
| 5,522,850 | 6/1996 | Yomtov et al. . |
| 5,535,752 | 7/1996 | Halperin et al. . |
| 5,545,186 | 8/1996 | Olson et al. . |
| 5,564,434 | 10/1996 | Halperin et al. . |
| 5,658,318 | 8/1997 | Stroetmann et al. . |
| 5,669,391 | 9/1997 | Williams . |
| 5,718,242 | 2/1998 | McClure et al. . |
| 5,732,708 | 3/1998 | Nau et al. . |
| 5,755,736 | 5/1998 | Gillberg et al. . |
| 5,776,168 | 7/1998 | Gunderson . |
| 5,931,857 | 8/1999 | Prieve et al. . |

* cited by examiner

Primary Examiner—George R. Evanisko
(74) Attorney, Agent, or Firm—Girma Wolde-Michael

(57) ABSTRACT

A monitoring device for implant in a patient's body and a method of its use. The monitoring device is provided with an electrogram amplifier, a sensing electrode coupled to the amplifier, and a memory for storing electrogram signals sensed by the electrogram amplifier. Responsive to detection of an arrhythmia, the monitor generates an internal electrogram storage trigger signal and initiates a patient trigger confirmation period. In response to receiving a patient trigger signal within the confirmation period, the monitor stores electrogram signals. The monitor preferably also defines an internal trigger confirmation period following a patient trigger signal and in response to an internal electrogram storage trigger signal within the internal trigger confirmation period, also stores electrogram signals.

17 Claims, 12 Drawing Sheets

METHOD AND APPARATUS FOR MONITORING HEART RATE

BACKGROUND OF THE INVENTION

The present invention relates generally to implantable medical devices and more particularly to implantable medical devices intended for use in monitoring a patient's heart rhythm.

Implantable pacemakers and cardioverters monitor the heart's rhythm in order to detect arrhythmias and deliver appropriate therapies to terminate detected arrhythmias. In conjunction with this function, the ability of the device is to store information with regard to monitored heart rhythms has dramatically increased over the past two years. Examples of implantable pacemakers and defibrillators and associated devices which have the capability of storing information related to monitor heart rhythms include U.S. Pat. No. 4,223,678, issued to Langer et al., U.S. Pat. No. 4,295,474 issued to Fischell, U.S. Pat. No. 4,625,730 issued to Fountain et al., U.S. Pat. No. 5,732,708 issued to Nau et al., U.S. Pat. No. 5,669,391 issued to Williams, U.S. Pat. No. 5,522,850 issued to Yomtov et al., U.S. Pat. No. 5,312,446 issued to Holschbach et al. and U.S. Pat. No. 5,776,168 issued to Gunderson, all incorporated herein by reference in their entireties. In addition, there have recently been developed subcutaneously implantable monitoring devices, which do not deliver any anti-arrhythmia therapies to the heart but simply store information regarding a patient's heart rhythms for later uplink to an external device. Such devices are disclosed in U.S. Pat. No. 5,331,966 issued to Bennett et al., U.S. Pat. No. 5,135,004 issued to Adams and U.S. Pat. No. 5,113,869 issued to Nappholz et al., all also incorporated herein by reference in their entireties.

In conjunction with implantable monitoring devices of the types discussed above, storage of information regarding episodes of arrhythmias is typically accomplished in response to either detection of an arrhythmia meeting pre-defined criteria, as described in the above-cited Langer, Yomtov and Nappholz patents, among others, or in response to a trigger signal received from the patient, typically provided by means of an external controller or activator, as disclosed in the above cited Bennett et al. patent. The above cited Fountain et al patent discloses a device having the capability of storing information related to episodes of arrhythmias in response to either a patient trigger or detection of an arrhythmia episode by the implanted device. U.S. Pat. No. 5,931,857 issued to Prieve et al. in particular discloses an implantable defibrillator, which confirms a patient's diagnosis of a need for therapy and in response, delivers the therapy. In the commercially marketed version of the device described in this patent, either confirmation of the patient's diagnosis of arrhythmia or detection of arrhythmia by the device may trigger storage of an associated electrogram.

While devices of the types discussed above are extremely valuable in monitoring the condition of a patient, automatic triggers for electrogram storage are subject to noise, particularly in the context of subcutaneous monitors, and as a result may record electrograms in response to events that are not actually arrhythmias. The use of manual triggers to trigger arrhythmia storage can result in inappropriate storage of electrogram data due to misperception by the patient, or alternatively can result in late initiation of electrogram storage due to a delay between onset of the arrhythmia and the point at which the patient perceives the symptoms of the arrhythmia. In this case in particular, late triggering may have result in the device failing to record the events that are associated with the onset of the arrhythmia, which are often of the most interest.

SUMMARY OF THE INVENTION

The present invention is directed toward an implantable device having enhanced capabilities for monitoring arrhythmia episodes over extended periods of time. The information collected by the implantable device is stored and telemetered to an associated external device such as a device programmer for display and analysis. In particular, the present invention provides an implantable monitor, which allows for a corroboration between the detection of the arrhythmias by the device and the occurrence of patient's symptoms. The invention provides the benefit of reducing the number of inappropriately stored electrocardiograms not actually indicative of arrhythmias and enables the device to record the onset of the arrhythmia, even in cases where the is a substantial delay between the onset of the arrhythmia and the onset of the patient's perceptible symptoms. The invention provides for the permanent storage of electrogram records associated in time with an electrogram storage trigger signal from the patient or a device generated internal electrogram storage trigger signal, in response to a confirming trigger signal thereafter of the other type, within a defined confirmation period.

In one embodiment, the implanted device may employ a looping memory as is described in the Langer patent cited above, wherein electrogram signals are continuously recorded in memory and overwritten, such that at any point in time, the electrogram signals corresponding to a proceeding period of time are stored, which time period may be for example, 10 or 20 seconds, up to a period of several minutes. The electrogram signals in the looping memory prior to and following the device and/or patient generated trigger signals may be permanently stored in an electrogram storage memory for later transmission to an external programmer or monitor. Transfer of the electrogram signals stored in the looping memory to the electrogram storage memory occurs in response to expiration of a defined record duration period, which may be timed from the trigger signal which initiated the confirmation period. In preferred embodiments, the electrogram signals present in the looping memory on expiration of the record duration period include signals occurring during a time interval initiated at a point preceding the trigger signal that initiated the confirmation period and extending for a defined period thereafter. In response to detection, during the confirmation period, of a confirming trigger signal of a type other than the trigger signal which initiated the confirmation period, the contents of the looping memory, previously or subsequently transferred to the electrogram storage memory are flagged as permanent and are not written over by subsequent electrogram records. The permanently stored electrogram records are available for later uplink to an external device.

The confirmation periods following patient trigger signals and internal trigger signals may be the same, or more preferably the confirmation periods following internal trigger signals may be substantially greater to allow for the fact that an arrhythmia may persist for minutes or hours prior to onset of the patient's symptoms. For example, the confirmation period following patient trigger signals will generally be in the range of up to a few minutes, while the confirmation period following device generated internal trigger signal may extend for up to a period of several hours. In some preferred embodiments, permanent storage of electrogram signals in response to a patient signal within the confirmation period following an internal trigger signal may also be pre-conditioned on a failure of the device to detect termination of the arrhythmia which caused the internal trigger signal.

DETAILED DESCRIPTION OF THE PREFERRED EMBODIMENTS

Figure 1:
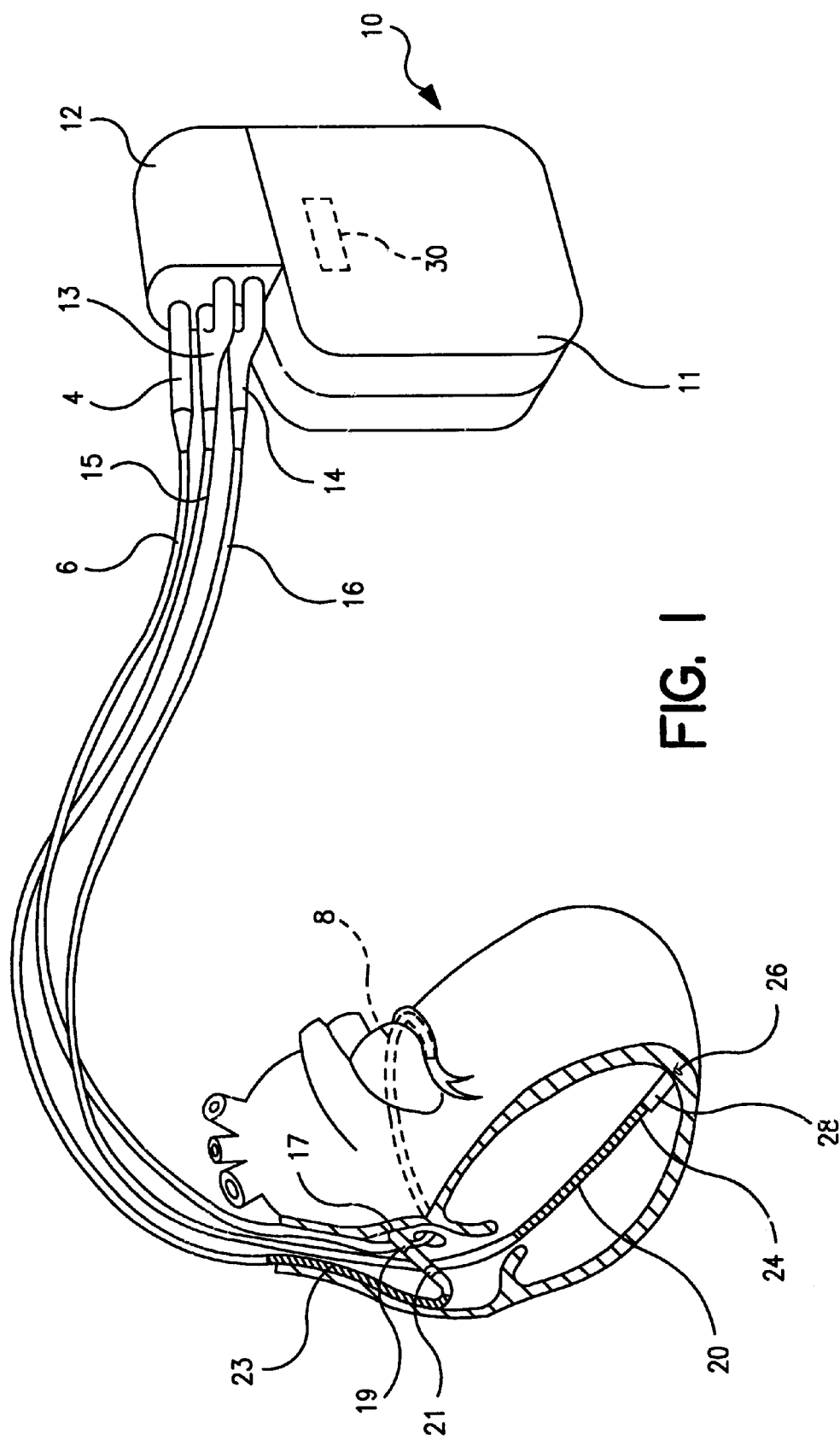
FIG. 1 illustrates an implantable pacemaker/cardioverter/defibrillator of a type useful in practicing the present invention, in conjunction with a human heart.

FIG. 1 illustrates a defibrillator and lead set of a type in which the present invention may usefully be practiced. The ventricular lead includes an elongated insulative lead body 16, carrying three mutually insulated conductors. Located adjacent the distal end of the lead are a ring electrode 24, an extendible helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14, which carries three electrical connectors, each connector coupled to one of the conductors.

The atrial/SVC lead includes an elongated insulative lead body 15, also carrying three mutually insulated conductors. Located adjacent the J-shaped distal end of the lead are a ring electrode 21 and an extendible helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13, which carries three electrical connectors, each connector coupled to one of the conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4 that carries an electrical connector, coupled to the coiled conductor.

The pacemaker/cardioverter/defibrillator 10 includes a hermetic enclosure 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12, which serves as a receptacle and electrical connector for receiving the connectors 4, 13 and 14 and for interconnecting the leads to the circuitry within enclosure 11. An activity sensor 30 is illustrated schematically by broken outline, and may be an accelerometer or a piezoelectric transducer. Sensor 30 may optionally be used for monitoring patient activity for use in detection of arrhythmias as well as for regulation of pacing rate based upon demand for cardiac output.

Optionally, insulation of the outward facing portion of the housing 11 of the pacemaker/cardioverter/defibrillator 10 may be provided or the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
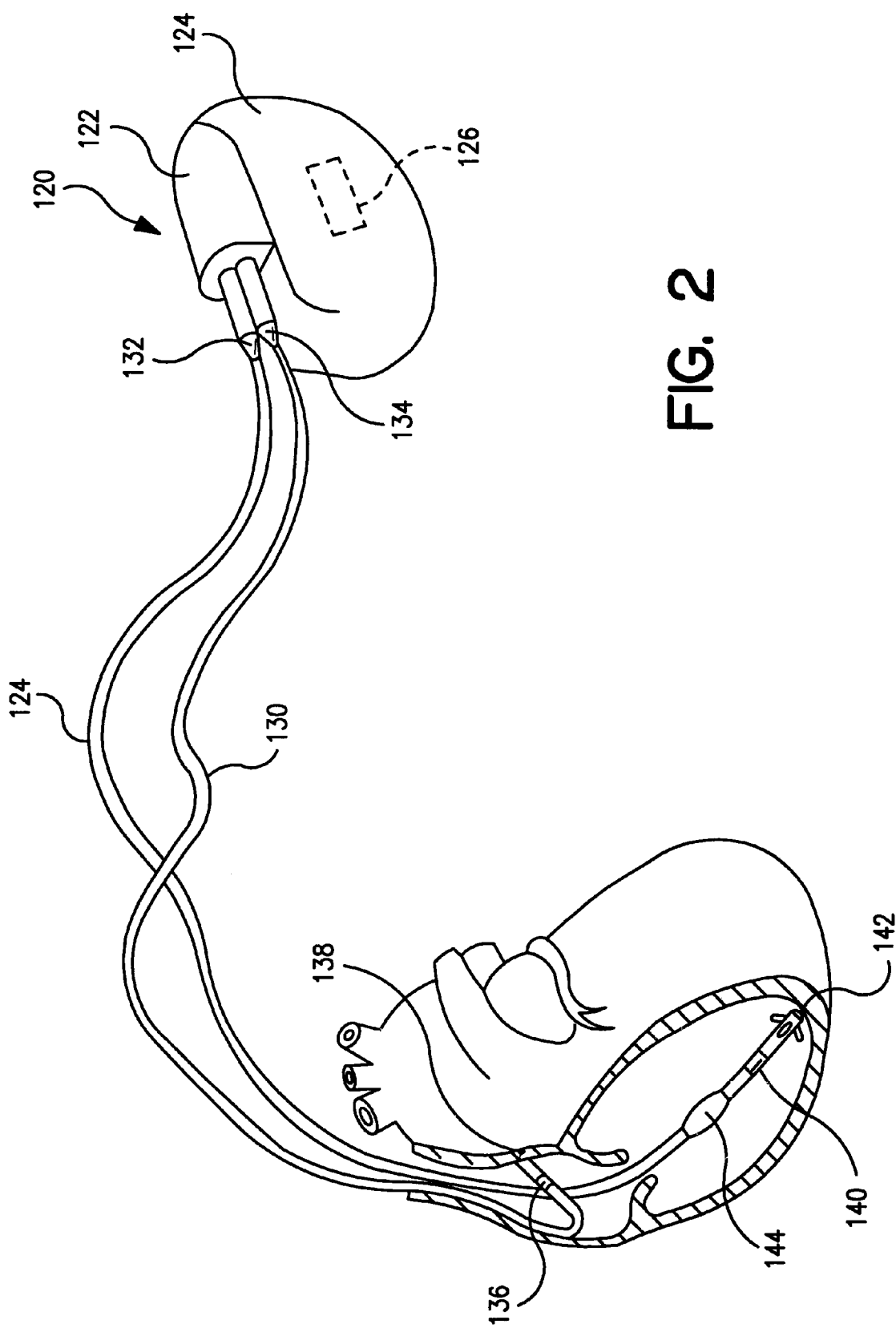
FIG. 2 illustrates an implantable pacemaker of a type useful in practicing the present invention, in conjunction with a human heart.

FIG. 2 illustrates a cardiac pacemaker of a type appropriate for use in practicing the present invention in conjunction with its associated lead system, illustrated in relation to a patient's heart. The pacemaker 120 includes a hermetic enclosure 124 containing the electronic circuitry used for generating cardiac pacing pulses and for monitoring the patient's heart rhythm. An activity sensor 126 is illustrated schematically by broken outline, and may be an accelerometer or a piezoelectric transducer as discussed above in conjunction with FIG. 1. Mounted to the enclosure 124 is a header 122 which serves as a receptacle and electrical connector for receiving the connectors 132 and 134 of pacing leads 128 and 130 and interconnecting the leads to the circuitry within enclosure 124. Lead 128 is a ventricular lead provided with electrodes 140 and 142 for monitoring right ventricular heart signals. Also illustrated on lead 128 is a physiologic sensor 144 which may optionally be included in addition to or as an alternative to the activity sensor 126, and which may take the form of an oxygen sensor, pressure sensor, temperature sensor, other sensor of any of the various types employed for monitoring demand for cardiac output or for measuring heart hemodynamics. Sensor 124 may be used in conjunction with or as an alternative to the activity sensor 126 for monitoring patient activity for use in detection of arrhythmias as well as for regulation of pacing rate based upon demand for cardiac output. Atrial lead 130 carries electrodes 136 and 138 and is employed for sensing and pacing the patient's atrium.

Figure 3:
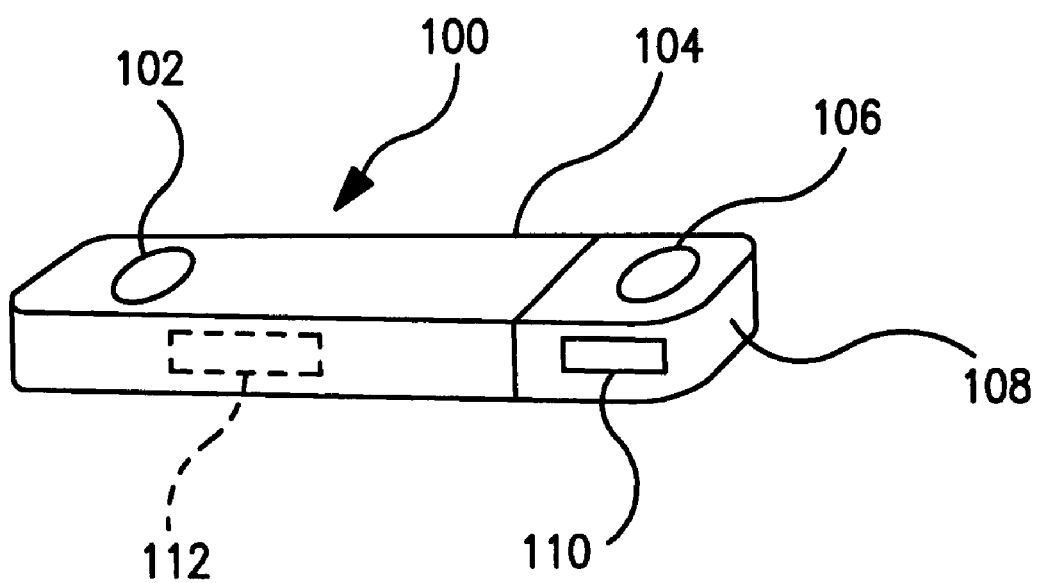
FIG. 3 illustrates an implantable monitor of a type useful in practicing the present invention.

FIG. 3 illustrates a subcutaneously implantable monitor of a type appropriate for use in practicing the present invention.

The monitor shares the external configuration of the Medtronic Reveal® implantable monitor, and is provided with a hermetically sealed enclosure 104 containing the electronic circuitry used for generating cardiac pacing pulses and for monitoring the patient's heart rhythm and which carries a molded plastic header 108. The enclosure 104 and the header 108 each carry an electrode 102 and 106, respectively for monitoring heart rhythm. Also mounted in the header 108 is an antenna 110 for use in communicating between the device and an external programmer. Illustrated in broken outline at 112 is an optional internal activity sensor, of the type typically employed in the context of rate responsive cardiac pacemakers, taking the form either of an accelerometer or a piezo-electric transducer, for use in detection of arrhythmias. Heart signals are detected between the electrodes 102 and 106 and measurements of physical activity are detected by sensor 112 for.

Figure 4:
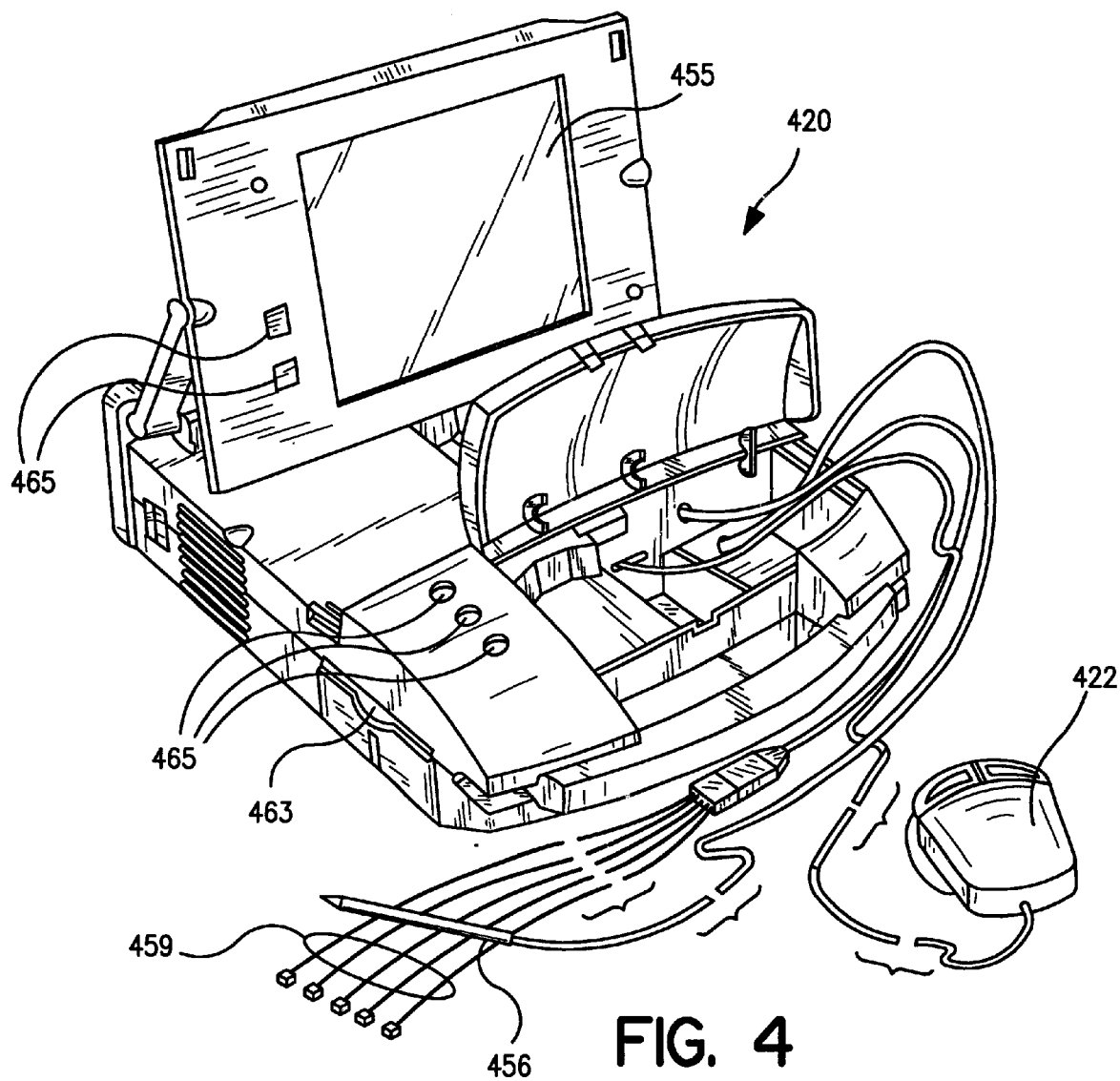
FIG. 4 is a perspective view of a programmer of a type useful in practicing the present invention.

FIG. 4 is a plan view of an external programmer of a sort appropriate for use in conjunction with the practice of the present invention in conjunction with any of the devices of FIGS. 1–3. The programmer 420 is a microprocessor controlled device which is provided with a programming head 422 for communicating with an implanted device, a set of surface electrogram electrodes 459 for monitoring a patient's electrogram, a display 455 which is preferably a touch sensitive display, control buttons or keys 465, and a stylus 456 for use in conjunction with the touch sensitive screen 455. By means of the control keys 465 and the touch sensitive screen 455 and stylus 456, the physician may format commands for transmission to the implantable device. By means of the screen 455, the physician may observe information telemetered from the implantable device. The programmer is further provided with a printer 463 which allows for hard copy records of displays of signals received from the implanted device such as stored parameters, programmed parameters and stored electrograms according to the present invention. While not visible in this view, the device may also be provided with a floppy disk or CD ROM drive and/or a port for insertion of expansion cards such as P-ROM cartridges, to allow for software upgrades and modifications to the programmer 420. In the context of the present invention, programmer 420 may serve simply as a display device, displaying electrograms stored by the implanted device or instead may receive uplinked electrograms for analysis prior to display.

Figure 5:
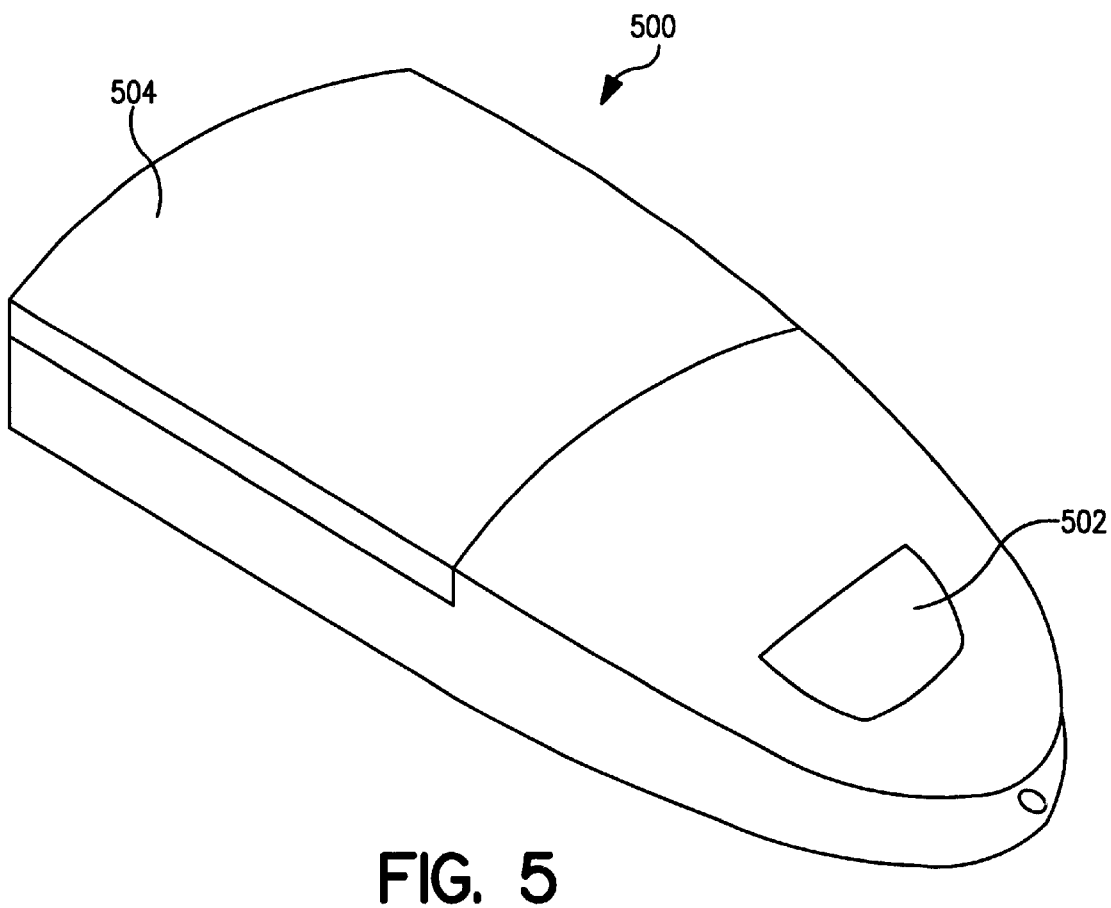
FIG. 5 is a perspective view of a patient activator of a type useful in practicing the present invention.

FIG. 5 illustrates the general physical configuration of a patient activator of a type that may be employed with the present invention. The activator 500 generally takes the form of a plastic enclosure provided with a push button 502 by which the patient may cause generation of an electrogram storage trigger for transmission to the implantable device. The device is battery powered, employing batteries accessible by means of the battery cover 504. On the reverse side of the device, not visible, are optional indicator lights that may be used to provide information to the patient with regard to the status and functioning of the implanted device in response to the patient trigger signal.

Figure 6:
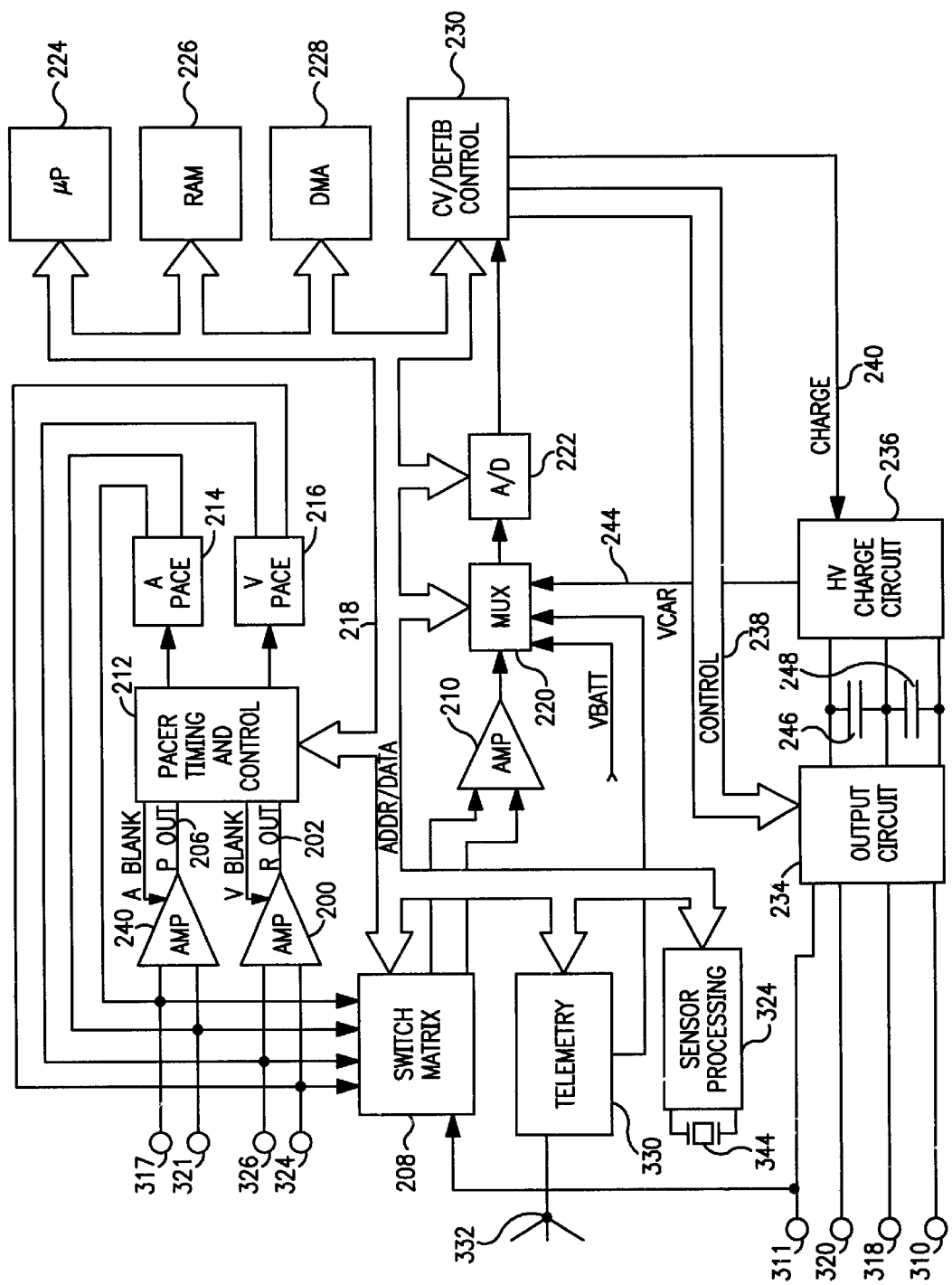
FIG. 6 is a functional schematic diagram of an implantable pacemaker/cardioverter/defibrillator of a type useful in practicing the present invention.

FIG. 6 is a functional schematic diagram of an implantable pacemaker/cardioverter/defibrillator of the type illustrated in FIG. 3, in which the present invention may usefully be practiced. This diagram should be taken as exemplary of one type of anti-tachyairhythmia device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

Telemetry circuit 330 receives downlink telemetry from and sends uplink telemetry to the programmer and patient activator by means of antenna 332. Data to be uplinked to the programmer and activator and control signals for the telemetry circuit are provided by microprocessor 224 via address/data bus 218. Received telemetry, including received patient trigger signals, is provided to microprocessor 224 via multiplexer 220. The atrial and ventricular sense amp circuits 200, 204 produce atrial and ventricular EGM signals, which also may be digitized and stored according to the present invention and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, which patent is hereby incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer as is and from a patient activator as discussed above.

The device of FIG. 6 may additionally be provided with an activity sensor 344, mounted to the interior surface of the device housing or to the hybrid circuit within the device housing. The sensor 344 and sensor present in circuitry 342 may be employed in the conventional fashion described in U.S. Pat. 4,428,378 issued to Anderson et al, incorporated herein by reference in its entirety, to regulate the underlying pacing rate of the device in rate responsive pacing modes and also serves as in an indicator of the patient's activity level for use in conjunction with detection of arrhythmias as disclosed in U.S. Pat. No. 5,330,505, issued to Cohen, incorporated herein by reference in its entirety.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with antitachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses and all of the intervals and period associated with electrogram storage according to the present invention. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including antitachyairrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with the present invention in conjunction with arrhythmia detection and arrhythmia termination detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 (FIG. 2) may be configured as a plurality of recirculating buffers, which define a looping memory capable of holding stored electrograms for use in practicing the present invention. A second portion of the memory 226 is configured as an electrogram storage memory for storing multiple electrogram records for later transmission to an external monitor or programmer.

The arrhythmia detection and arrhythmia termination detection methods employed in conjunction with the present invention may include any of the numerous available prior art arrhythmia and termination detection algorithms known top the art. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various other arrhythmia and termination detection methodologies known to the art might also be employed, for example including those described in the patents cited above as well as those described in U.S. Pat. No. 5,489,293, issued to Pless et al., U.S. Pat. No. 5,179,947, issued to Weiss, U.S. Pat. No. 5,251,626, issued to Nickolls et al., U.S. Pat. No. 5,184,615, issued to Nappholz et al., U.S. Pat. No. 5,273,049, issued to Steinhaus et al., U.S. Pat. No. 5,658,318, issued to Stroetmann et al., U.S. Pat. No. 5,718,242, issued to McClure et al, and U.S. Pat. No. 5,431,685, issued to Alt, all incorporated herein by reference in their entireties.

In the event that an atrial or ventricular tachyarrhythmia is detected, and an anti-tachyarrhythmia pacing regimen is desired, timing intervals for controlling generation of antitachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 7:
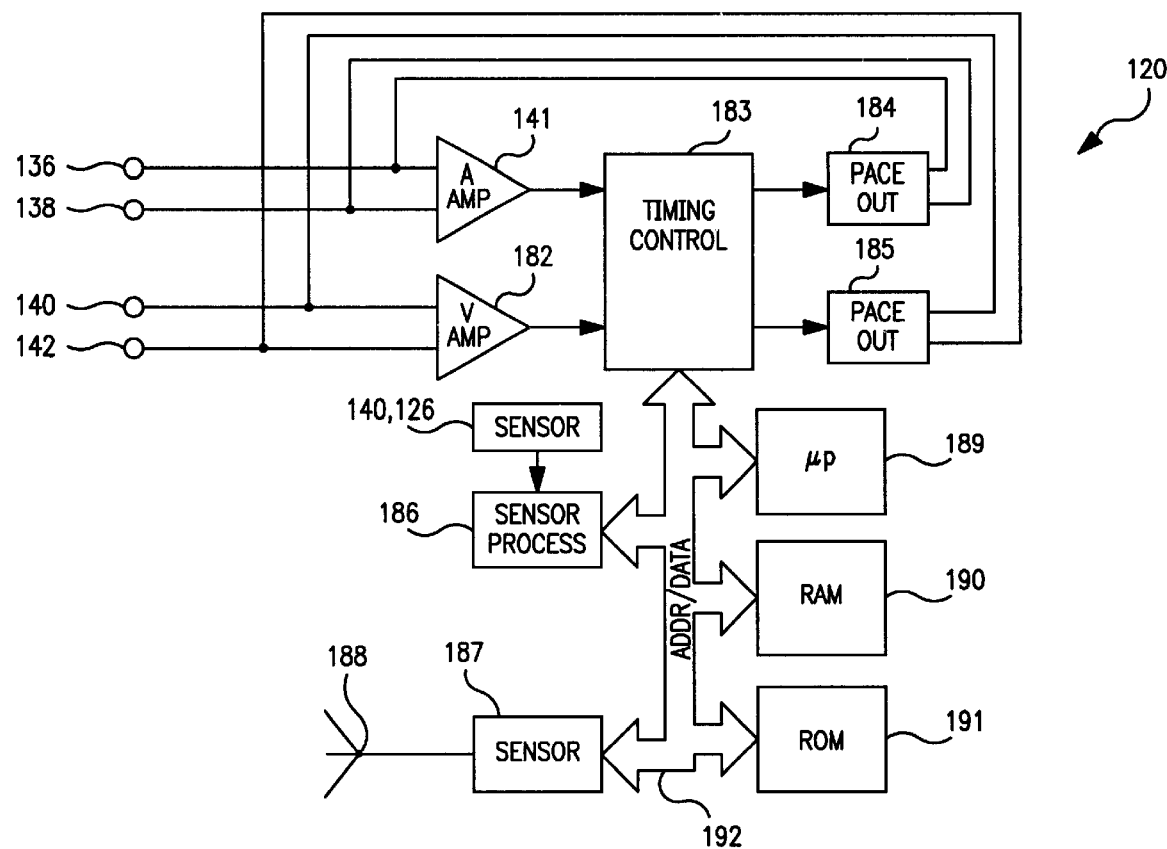
FIG. 7 is a functional schematic diagram of an implantable pacemaker of a type useful in practicing the present invention.

FIG. 7 is a functional schematic diagram of the pacemaker 120 illustrated in FIG. 2. The pacemaker of FIGS. 2 and 6 is essentially a set of sub-components of the implantable pacemaker/cardioverter/defibrillator illustrated in FIGS. 1 and 5. Like the device of FIG. 5, the pacemaker is a microprocessor-controlled device with microprocessor 189 operating under control of programming stored in Read Only Memory (ROM) 191. Random Access Memory (RAM) 158 corresponds to memory 226 (FIG. 6) and serves to store electrogram records according to the present invention. In the device as illustrated, electrodes 136 and 138, intended for location in the atrium of the patient's heart are coupled to an atrial amplifier 181 which may correspond to atrial amplifier 204 in FIG. 6. Similarly, ventricular electrodes 140 and 142 are coupled to ventricular amplifier 182, which may correspond to ventricular amplifier 200 in FIG. 6. The outputs of atrial and ventricular amplifiers 181 and 182 are input into timing and control circuitry 183 which conforms generally to the pacer timing and control circuitry 212 of FIG. 6, and which measures intervals between detected depolarizations and controls intervals between delivered pacing pulses as well as generating interrupts via data/address 192 to awake microprocessor 189 in response to delivery of a pacing pulse or sensing of a cardiac depolarization. Intervals between depolarizations measured by timing/control circuitry 183 are stored in Random Access Memory (RAM) 190 until processed by microprocessor 189. Random Access Memory (RAM) 158 corresponds to memory 226 (FIG. 6) and serves to store electrogram records according to the present invention under control of microprocessor 189, in the same manner as described above in conjunction with FIG. 6. Atrial and ventricular pacing pulses delivered according to one or more of the standard pacing modes described in conjunction with FIG. 6 are produced by atrial and ventricular pulse generator circuits 184 and 185 which may correspond to pulse generator circuits 215 ad 216 in FIG. 6.

The sensor illustrated in FIG. 7 may correspond to either an activity sensor 126 as described in conjunction with FIG. 2 above or to a hemodynamic sensor 140, as described in conjunction with FIG. 2. If the sensor is an activity sensor, then sensor-processing circuitry 186 may correspond to sensor processing circuitry 342 discussed in conjunction with FIG. 6. However, if the sensor is a hemodynamic sensor, the sensor processing circuitry would correspond to the sort of processing circuitry typically associated with hemodynamic sensors. For purposes of the present invention, the hemodynamic sensor may be, for example, an oxygen saturation sensor in conjunction with associated processing circuitry as described in U.S. Pat. No. 5,176,137 issued to Erickson et al., a pressure sensor and associated sensor processing circuitry as described in U.S. Pat. No. 5,564,434 issued to Halperin et al., an impedance sensor and associated sensor processing circuitry as described in U.S. Pat. No. 4,535,774 issued to Olson, or a temperature sensor and associated processing circuitry as described in U.S. Pat. No. 5,535,752 issued to Halperin et al, all incorporated herein by reference in their entireties, or may correspond to other types of physiologic sensors, as may be appropriate, including those discussed in the above cited Cohen patent. Telemetry circuitry 187 in conjunction with antenna 188 serves to transmit information to and receive information from an external programmer or patient activator precisely as described above in conjunction with the device of FIG. 6.

Figure 8:
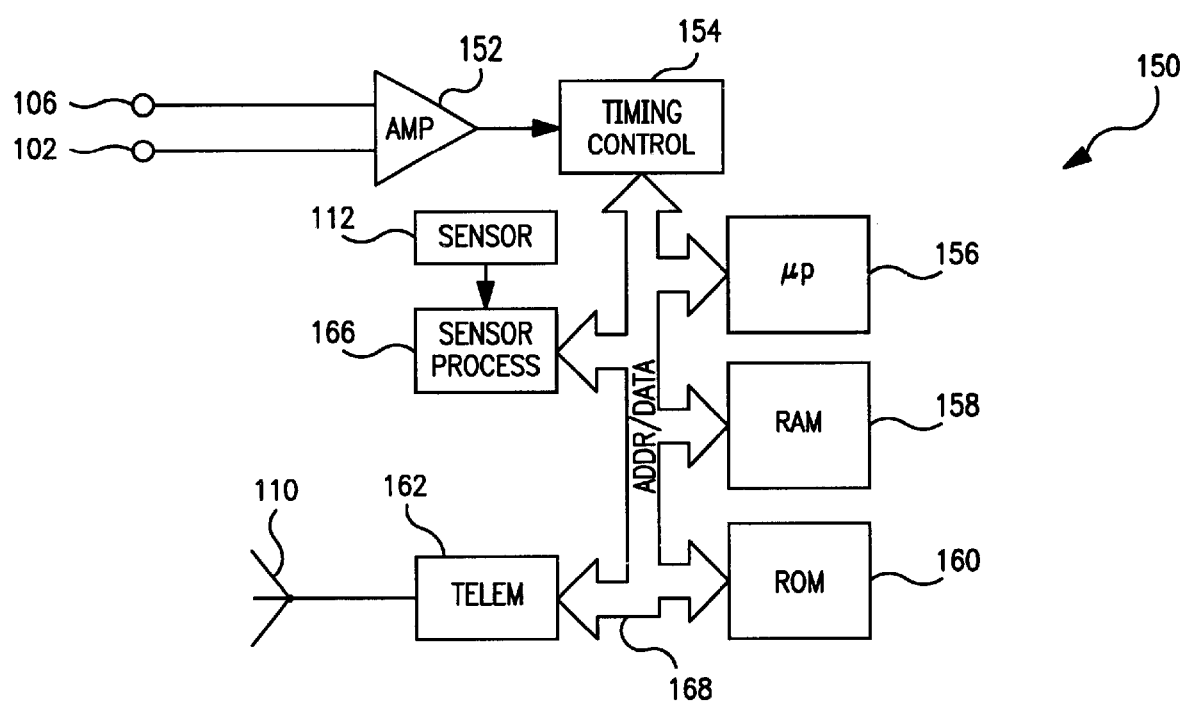
FIG. 8 is a functional schematic diagram of an implantable monitor of a type useful in practicing the present invention.

FIG. 8 illustrates the functional organization of the subcutaneously implantable heart monitor 100 illustrated in FIG. 3. This device consists essentially of a set of sub-components of the more complex embodiment of the invention disclosed in FIG. 6, and includes a sense amplifier 152 coupled to electrodes 102 and 106, illustrated in FIG. 1. Sense amplifier 152 may correspond to sense amplifier 204 or 200 in FIG. 6. Like the device of FIG. 6, the implantable monitor may be a microprocessor controlled device operating under control microprocessor 156 with its functionality controlled primarily by software stored in the read only memory associated therewith. In this context, amplifier 152 detects the occurrence of heart depolarizations, with timing/control circuitry 154 serving to measure the durations between the detected heart depolarizations and to generate interrupts awakening microprocessor 156 so that it may store, analyze and process the detected intervals. Random Access Memory (RAM) 158 corresponds to memory 226 (FIG. 6) and serves to store electrogram records according to the present invention in the same manner as described in conjunction with FIG. 6. Like the device in FIG. 6, timing and control circuitry communicates with the microprocessor and the remaining circuitry by means of the address/data bus 168. Telemetry system 162 may correspond to telemetry system 330 in FIG. 6 and, via antenna 110 transmits and receives information from the external programmer and the patient activator. Sensor 112 may correspond to sensor 344 in FIG. 6 and it may be a physical activity sensor as discussed above. The output of sensor 112 is passed through sensor processing circuitry 166 which may correspond to sensor processing circuitry 342 in FIG. 6.

Figure 9:
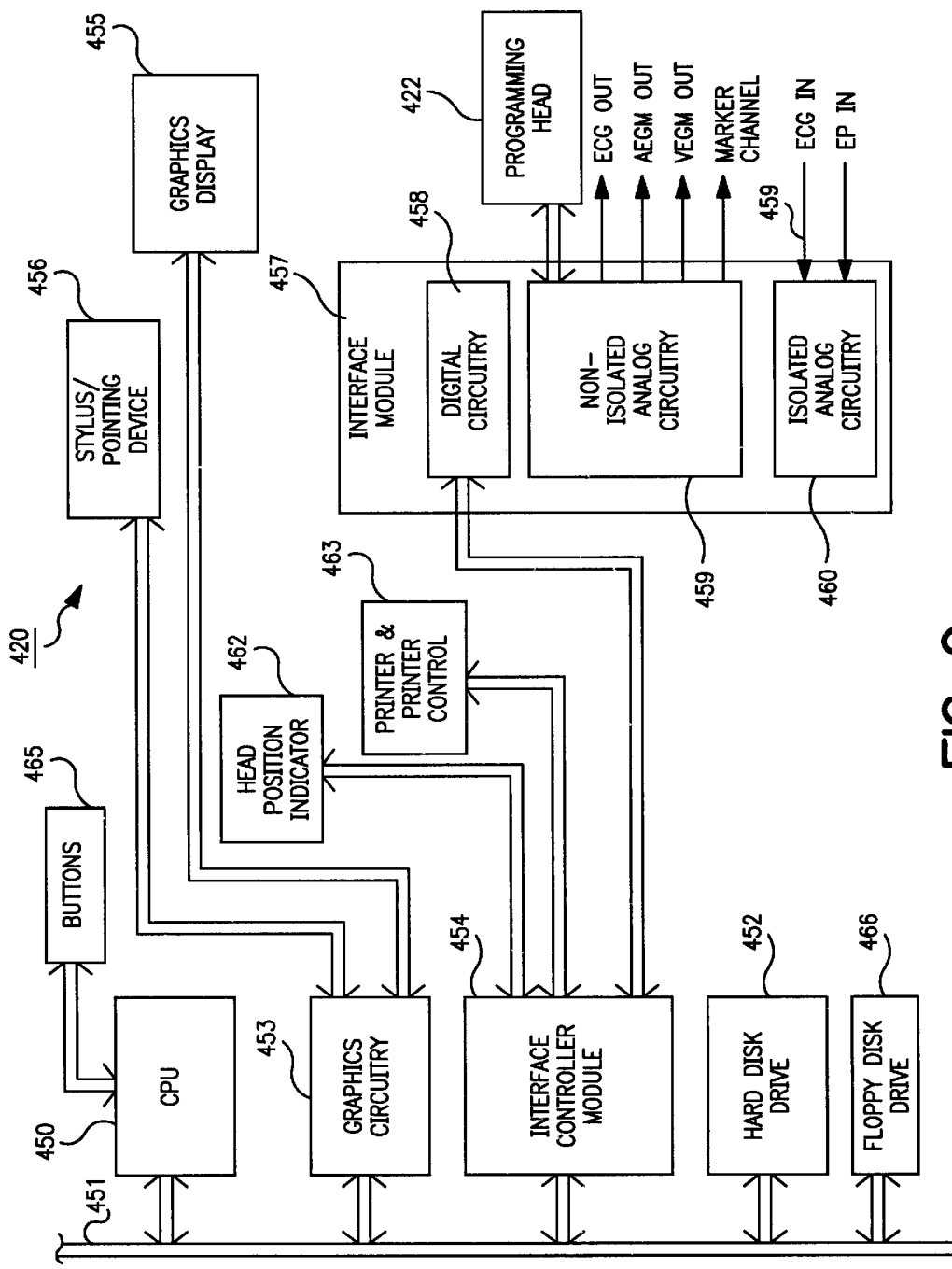
FIG. 9 is a functional schematic diagram of a programmer of a type useful in practicing the present invention.

FIG. 9 is a finctional schematic of a programmer as illustrated in FIG. 4, appropriate for use in conjunction with the invention. Programmer 420 is a personal computer type, microprocessor-based device incorporating a central processing unit 450, which may be, for example, an Intel 80386 or 80486 or Pentium microprocessor or the like. A system bus 451 interconnects CPU 450 with a hard disk drive 452 storing operational programs and data and with a graphics circuit 453 and an interface controller module 454. A floppy disk drive 466 or a CD ROM drive is also coupled to bus 451 and is accessible via a disk insertion slot within the housing of the programmer 420. Programmer 420 further comprises an interface module 457, which includes digital circuit 458, non-isolated analog circuit 459, and isolated analog circuit 460. Digital circuit 448 enables interface module 457 to communicate with interface controller module 454.

In order for the physician or other caregiver or user to communicate with the programmer 420, control buttons 465 or optionally a keyboard coupled to CPU 50 is provided. However the primary communication mode is through graphics display screen 455 of the "touch sensitive" type controlled by graphics circuit 453. A user of programmer 420 may interact therewith through the use of a stylus 456, also coupled to graphics circuit 453, which is used to point to various locations on screen 455, which display menu choices for selection by the user or an alphanumeric keyboard for entering text or numbers and other symbols.

Graphics display 455 also displays a variety of screens of telemetered out data or real time data including electrogram records stored according to the present invention. Programmer 420 is also provided with a strip chart printer 463 or the like coupled to interface controller module 454 so that a hard copy of a patient's electrogram, EGM, marker channel or of graphics displayed on the display 455 can be generated.

As will be appreciated by those of ordinary skill in the art, it is often desirable to provide a means for programmer 20 to adapt its mode of operation depending upon the type or generation of implanted medical device to be programmed. Accordingly, it may be desirable to have an expansion cartridge containing EPROM's or the like for storing software programs to control programmer 420 to operate in a particular manner corresponding to a given type or generation of implantable medical device. In addition, in accordance with the present invention, it is desirable to provide the capability through the expansion cartridge or through the floppy disk drive 66 or CD ROM drive.

The non-isolated analog circuit 459 of interface module 457 is coupled to a programming head 422, which is used to establish the uplink and downlink telemetry links between the pacemaker 410 and programmer 420 as described above. Uplink telemetered EGM signals are received in programming head 422 and provided to non-isolated analog circuit 459. Non-isolated analog circuit 459, in turn, converts the digitized EGM signals to analog EGM signals and presents these signals on output lines A EGM OUT and V EGM OUT. These output lines may then be applied to a strip-chart recorder 463 to provide a hard-copy printout of the A EGM or V EGM for viewing by the physician. Similarly, the markers received by programming head 422 are presented on the MARKER CHANNEL output line from non-isolated analog circuit 459.

Isolated analog circuit 460 in interface module 547 is provided to receive external electrogram and electrophysiologic (EP) stimulation pulse signals. In particular, analog circuit 460 receives electrogram signals from patient skin electrodes 459 and processes these signals before providing them to the remainder of the programmer system in a manner well known in the art. Circuit 460 further operates to receive the EP stimulation pulses from an external EP stimulator for the purposes of non-invasive EP studies, as is also known in the art.

In order to ensure proper positioning of programming head 422 over the antenna of the associated implanted device, feedback is provided to the physician that the programming head 422 is in satisfactory communication with and is receiving sufficiently strong RF signals. This feedback may be provided, for example, by means of a head position indicator, e.g. a light-emitting diode (LED) or the like that is lighted to indicate a stable telemetry channel.

Figure 10:
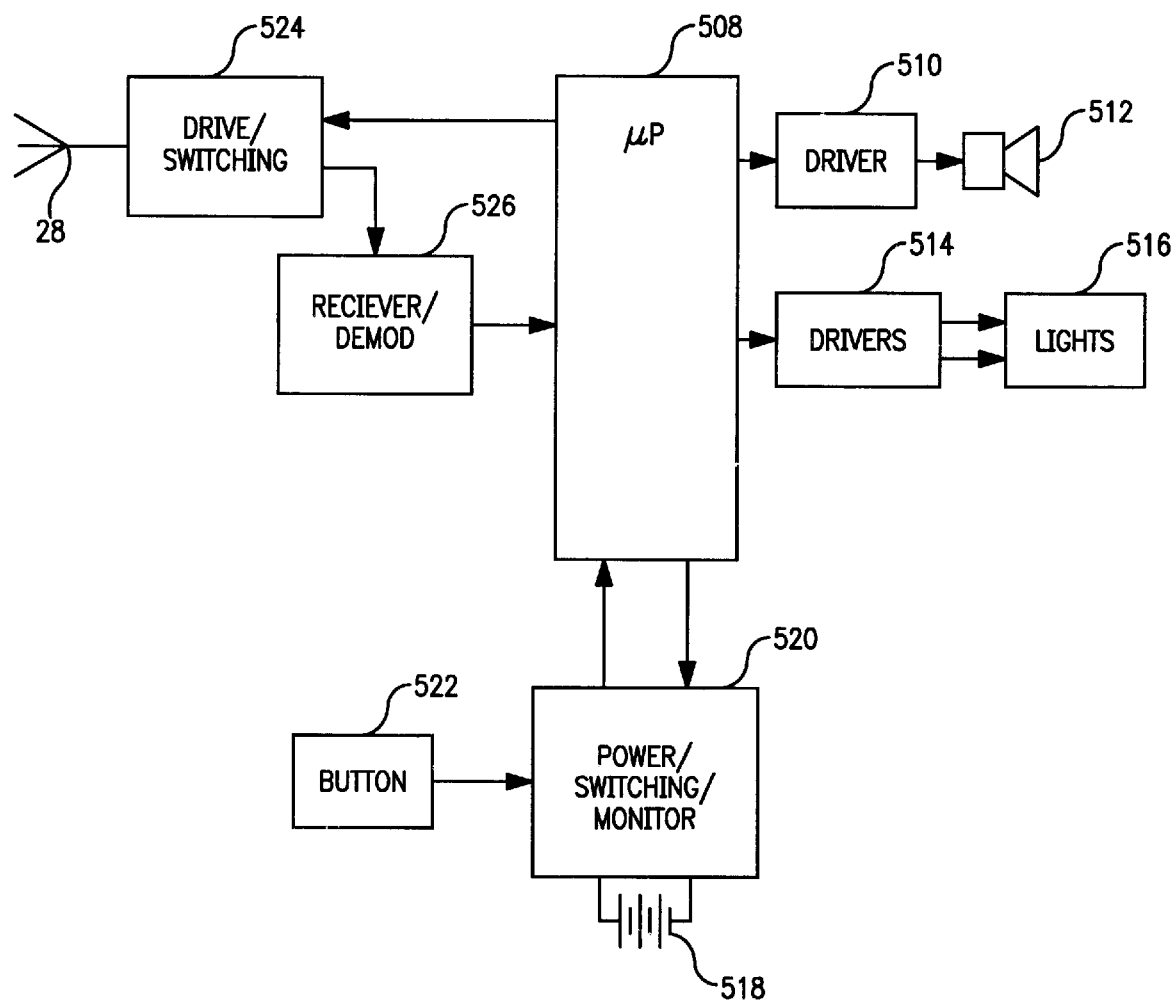
FIG. 10 is a functional schematic diagram of a patient activator of a type useful in practicing the present invention.

FIG. 10 is a block finctional diagram of a patient activator of a type appropriate for use in conjunction with the present invention. This device corresponds generally to patient activators presently available commercially for use in conjunction with implanted Medtronic pacemakers, and in particular, corresponds generally to the Medtronic Model-9462 patient activator presently in commercial distribution for use in conjunction with implanted bradycardia pacers. Control functions are provided by microprocessor 508, based upon programming stored in its associated read-only memory located therein. Microprocessor 508 may optionally provide output signals for producing audible patient alert signals by means of driver 510 and speaker 512. Microprocessor 108 may also optionally provide control signals to LED driver 514 to power the LEDs 516, referred to above. The speaker and/or the LEDs may be employed to signal the patient, for example, whether an electrogram record will be stored in response to a preceding patent trigger signal, so that the patient may arrange for the stored electrogram record to be reviewed by a physician. The device is powered by a battery 518 which is coupled to the microprocessor 508 by means of power/switching/battery monitor circuitry 520, which also provides the microprocessor with an indication that push button 502 has been pressed.

Communication with microprocessor 508 is accomplished by means of the antenna driver/switching circuit 524, the receiver demodulator 526 and RF antenna 128. Transmissions from the implanted device are received by antenna 528, and are demodulated by receiver demodulator 526 to be provided to the microprocessor. In response to received transmissions from the implanted device, the microprocessor controls operation of the audio and light drivers 510 and 514 to indicate the nature of the communication received. In response to activation of the push button 502, patient trigger signals for electrogram storage for transmission to the implanted device are provided by microprocessor 508 to the antenna drive/switching circuit, which then communicates with the implanted device by means of antenna 528.

Although the mechanism for generating a patient trigger signal as discussed above employs a telemetry transmitter, other mechanisms for communicating with an implanted device may be substituted. For example, if the implanted device includes an activity sensor as discussed above, the sensor may serve as a mechanism for receiving patient activation signals generated by the patient tapping the implanted device in a pre-defined manner, such as a series of three equally spaced firm taps. Alternatively, the device may be provided with an audio receiver as described in U.S. Pat. No. 5,433,736, issued to Arne et al. and incorporated herein by reference in its entirety. In such an embodiment, DTMF tones generated by a patient activator, for example, may be employed as patient trigger signals. Other mechanisms for signaling to the implanted device that the patient believes an arrhythmia is underway may also be employed.

Figure 11:
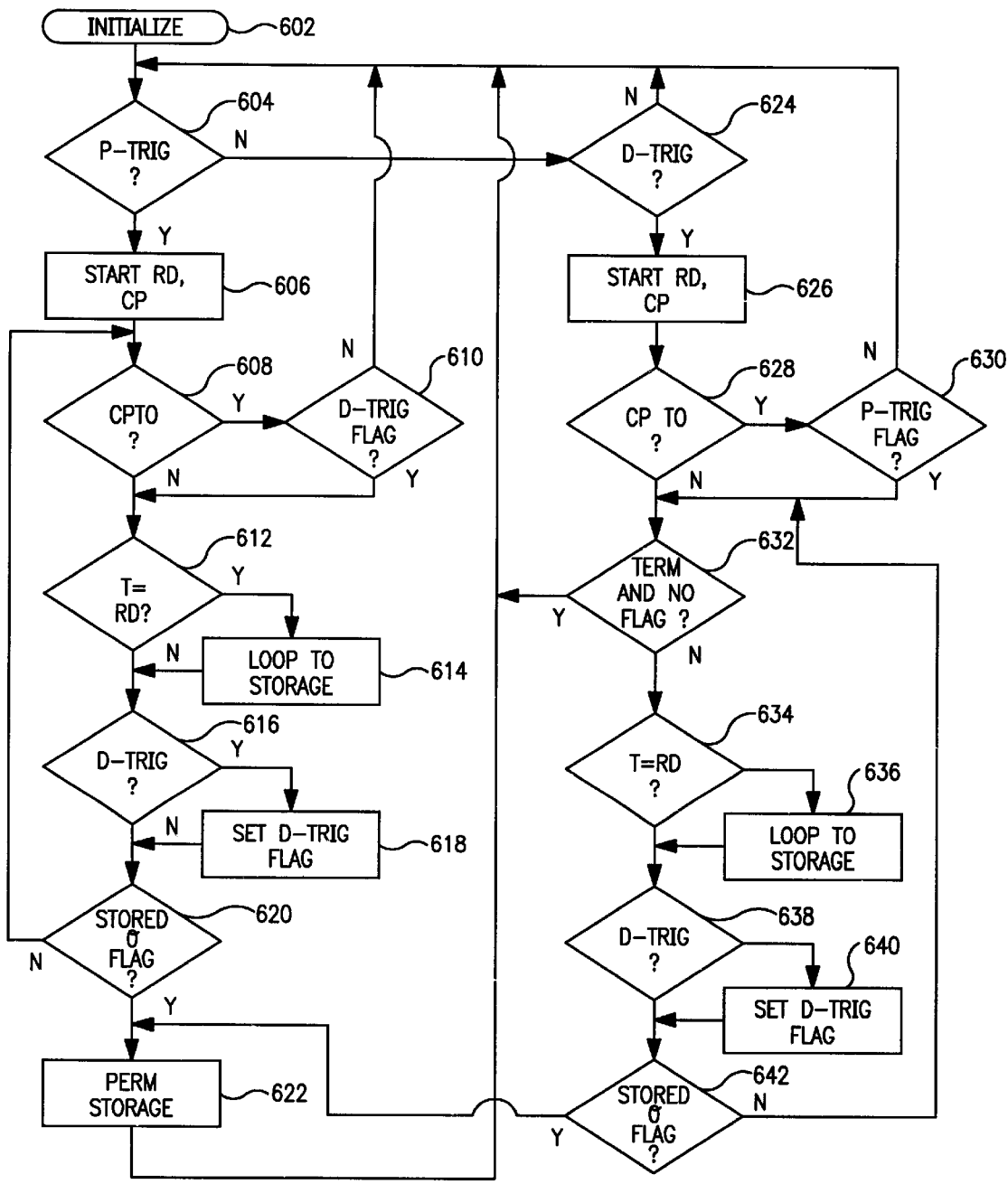
FIG. 11 is a functional flow chart illustrating a first method of electrogram storage, which may be employed in conjunction with the present invention.

FIG. 11 is a functional flow chart illustrating overall operation of a first embodiment of the present invention, which permanently stores electrogram signals in response to the occurrence of a patient trigger signal and an internal device trigger signal within a defined confirmation period of one another. In this embodiment, the random access memory of the implantable device is preferably configured to include a first set of addresses configured as a looping memory which operates continuously and a second set of addresses which provides an electrogram storage memory which may contain multiple electrogram records, each extending over the period of time over which the looping memory stores electrogram signals.

After initialization of the device at 602, the device awaits receipt of a patient trigger signal at 604 or a device initiated internal trigger signal at 624. In response to a received patient's trigger signal, the device initiates the record duration (RD) period, (the expiration of which marks the endpoint of the electrogram record) and the confirmation period (CP) at 606. Preferably, the looping memory is sized and the record duration period is defined such that the information in the looping memory on expiration of the record duration period extends from a time prior to the trigger signal that initiated the confirmation period. The device then awaits time out of the confirmation period at 608, time out of the record duration period at 612, or receipt of an internal device trigger signal at 616, which events may occur in any order, depending on the durations defined for the confirmation period and record duration period. If the confirmation period times out at 608, prior to receipt of an internal device trigger signal as indicated at 610, the device simply awaits the next subsequent patient trigger or device trigger signal at 604 or 624 and no electrogram record is permanently stored. Any electrogram records previously transferred from the looping memory to the electrogram storage memory will not be flagged for permanent storage and may be written over by subsequent electrogram records.

If, on the other hand, the confirmation period times out after receipt of a confirming device generated internal trigger signal at 610, or the confirmation period has not timed out at 608, the device continues to await expiration of the record duration period at 612 (assuming it has not previously expired) and generation of an internal trigger signal (assuming it has not previously occurred). In response to expiration of the record duration period at 612, the device transfers the electrogram signals stored in a looping memory to the electrogram storage memory at 614. In response to receipt of a device internal trigger signal at 616, the device sets a flag at 618 indicative of receipt of a device trigger signal. At 620, responsive to both the termination of the record duration period and the occurrence of a device generated internal trigger signal prior to confirmation period time-out, the device determines that a permanent electrogram record is to be stored. The electrogram record previously transferred from the looping memory is flagged as permanently stored and will not be overwritten by subsequent electrogram records.

In conjunction with the flow chart of FIG. 11, it should be understood that the receipt of the device internal trigger signal may occur before or after expiration of the record duration period at 612, and that while it is anticipated that the confirmation period will generally extend beyond expiration of the record duration period, this need not be so. A device according to the present invention creates a permanent electrogram record associated with a patient trigger signal for later telemetry in response to occurrence of a confirming internal flag within the confirmation period, regardless of whether the record duration interval expires before or after the confirmation period.

In response to a device generated internal trigger signal at 624, not preceded by a patient trigger signal within the defined confirmation interval, the device starts the record duration (RD) period and confirmation period (CP) at 626. In this case, confirmation period may be prolonged, for example extending up to a period of several hours, as some arrhythmias may persist for an extended period of time prior to onset of a patient's symptoms and a possibility of confirmation of the device internal trigger signal. In the event that the confirmation period times out at 628 prior to receipt of a confirming patient trigger signal, at 630, the device simply returns to await the next subsequent patient trigger signal at 604 or device trigger signal at 624 and no electrogram record is permanently stored. Any electrogram records previously transferred from the looping memory to the electrogram storage memory will not be flagged for permanent storage and may be written over by subsequent electrogram records.

In the event that the confirmation period has not timed out at 628, or in the event that the confirmation period has timed out following receipt of a patient trigger signal, the device checks at 632 to determine whether termination of the arrhythmia that initiated the device internal trigger signal has been detected without prior receipt of a patient trigger signal. If so, the device simply returns to await the next subsequent patient trigger or device trigger signal at 604 and 624, respectively, and no electrogram record is permanently stored. Any electrogram records previously transferred from the looping memory to the electrogram storage memory will not be flagged for permanent storage and may be written over by subsequent electrogram records. Unless the arrhythmia terminates prior to receipt of a patient trigger signal, the device checks for expiration of the record duration period at 634 and occurrence of a patient trigger signal at 638. In response to expiration of the record duration interval at 634, the contents of the looping memory are transferred to storage at 636. In response to detection of a patient trigger signal at 638 during the confirmation period, a flag indicating the occurrence of the P trigger signal is set at 640. In response to the expiration of the record duration period and the setting of the patient trigger flag at 640 during the confirmation period, the electrogram signal in the storage memory is designated for permanent storage at, allowing for later uplink to an external device.

In conjunction with the flow chart of FIG. 11, it should be understood that following a device internal trigger signal, in response to occurrence of a patient trigger signal during the confirmation period, and in the absence of detection of termination of the arrhythmia during the confirmation period, an electrogram record is designated for permanent storage for later uplink. As in conjunction with the events following an initial patient trigger signal at 604, described above, the patient's trigger signal at 638 and the expiration of the record duration period at 634 may occur in either order. In the context of the present invention, it is generally envisioned that the confirmation period following a device trigger signal will be sufficiently long that it will expire substantially after expiration of the record duration period. However, in the case of arrhythmias in which the onset of patient symptoms is relatively rapid, this need not be the case, and the record duration interval in such case may expire prior to the confirmation period.

In the embodiment of FIG. 11, the occurrence of multiple trigger signals of the same type within a single confirmation period does not result in restarting of the confirmation period. However, as illustrated in FIG. 12, in alternative embodiments of the present invention, successive trigger signals of the same type may alternatively result in resetting of the confirmation period and the record duration period.

Figure 12:
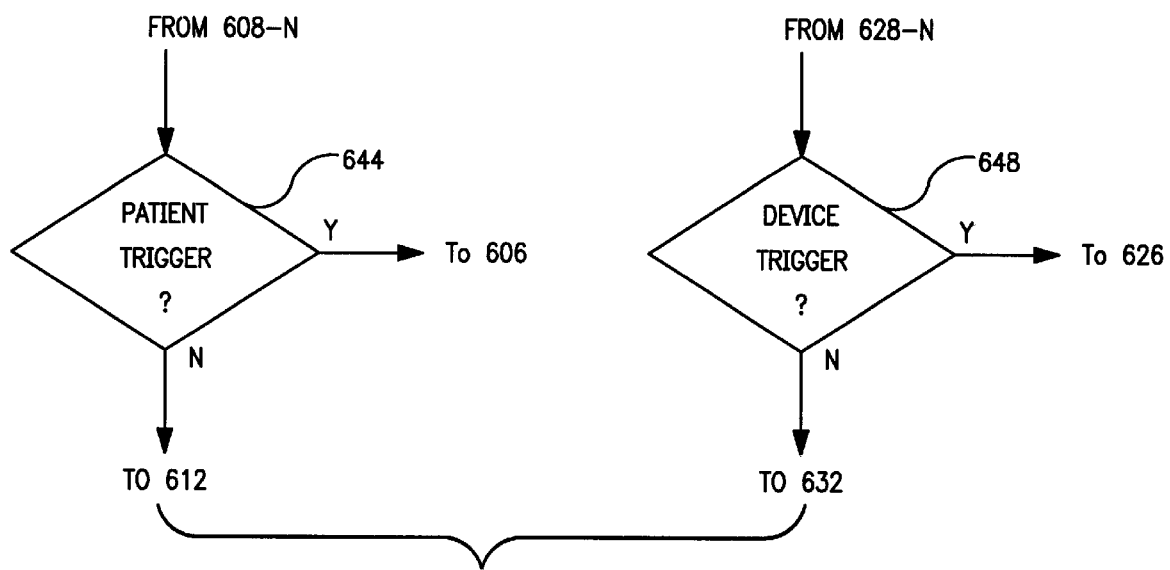
FIG. 12 is a functional flow chart illustrating a second method of electrogram storage, which may be employed in conjunction with the present invention.

FIG. 12 sets forth optional additions to the functional flow chart of FIG. 11, allowing the device to respond in a different fashion to multiple occurrences of the same type of trigger signal during a single confirmation period. As illustrated, in response to a determination that the confirmation period has not timed out at 608 following an initial patient trigger signal, detection of a subsequent patient trigger signal at 644 may cause the device to reset the record duration period and confirmation period at 606. Similarly, prior to expiration of the confirmation period following a device internal trigger signal at 624, in response to a subsequent device trigger signal at 648, the device may reset the record duration periods and confirmation periods at 626. Depending upon the particular arrhythmias being employed to trigger storage of electrogram records, one, either, or both of blocks 644 and 648 may optionally be added to the flow chart of FIG. 11.

The embodiment of FIG. 12 has the advantage that in the event that the initial trigger signal is erroneously generated, a correctly generated subsequent trigger signal of the same type will have the benefit of the full confirmation period, increasing the likelihood that electrogram records will be generated for actual arrhythmia episodes. For example, the device may erroneously detect the occurrence of an arrhythmia and, subsequently thereafter, correctly detect the occurrence of an arrhythmia, followed by onset of patient symptoms within a time period greater than the confirmation period from the first detection of the arrhythmia by the device, but less than the confirmation period following the second detection of the arrhythmia by the device.

While the embodiments disclosed above operate under the assumption that the looping memory runs continuously, it is also within the scope of the present invention to employ a looping memory which is activated intermittently, for example in response to events or sequences of events which indicate an increased likelihood of arrhythmia occurrence, such as might be indicated by an increased frequency of PVC's, as sensed by the implanted device or changes in the morphology of the S-T segment, as sensed by the implanted device. In addition, while the embodiments described above are based on the assumption that the stored electrogram record will include digitized electrogram signals, in some embodiments, as an alternative or in addition to the digitized electrogram the device may store a more condensed electrogram record, including the interval between sensed depolarizations of heart chambers, the amplitudes, widths or other characteristics of the sensed depolarizations, and the like. As such, the above disclosure should be considered exemplary rather than limiting in conjunction with the claims, which follow.

In conjunction with the above disclosure, I claim:

1. A monitoring device for implant in a patient's body, comprising:

an electrogram amplifier;

a sensing electrode coupled to the amplifier;

means for generating an internal electrogram storage trigger signal;

means for receiving a patient trigger signal;

means for defining the patient trigger confirmation period following an internal electrogram storage trigger signal; and storage means responsive to receipt of the patient trigger signal within the patient trigger confirmation period, for storing electrogram signals.

2. A device according to claim 2, further comprising:

means for defining an internal trigger confirmation period following the patient trigger signal; and storage means responsive to receipt of an internal electrogram storage trigger signal within the internal trigger confirmation period, for storing electrogram signals.

3. A device according to claim 1 or claim 2 wherein the means for generating an internal electrogram storage trigger signal comprises means for detecting a cardiac arrhythmia, coupled to the amplifier and wherein the means for generating the internal trigger signal is responsive to detection of the cardiac arrhythmia.

4. A device according to claim 3 wherein the means for receiving a patient trigger signal comprises a telemetry receiver.

5. A device according to claim 3 wherein the means for receiving a patient trigger signal comprises a sensor.

6. A device according to claim 5 wherein sensor comprises an activity sensor.

7. A device according to claim 1 or claim 2 wherein the device further comprises a physiologic sensor and wherein the means for generating an internal electrogram storage trigger signal comprises means for detecting a cardiac arrhythmia, coupled to the sensor, and wherein the means for generating the internal trigger signal is responsive to detection of the cardiac arrhythmia.

8. A device according to claim 7 wherein the means for receiving a patient trigger signal comprises a telemetry receiver.

9. A device according to claim 7 wherein the means for receiving a patient trigger signal comprises a sensor.

10. A device according to claim 9 wherein the sensor comprises an activity sensor.

11. A device according to claim 1 or claim 2 wherein the means for generating an internal electrogram storage trigger signal comprises means for detecting a cardiac arrhythmia and means for generating the internal trigger signal responsive to detection of a cardiac arrhythmia and further comprising means for detection of termination of an arrhythmia and means responsive to the detection of termination of an arrhythmia following generation of an internal electrogram storage signal, prior to receipt of a patient trigger signal, for preventing storage of electrogram signals.

12. A method of monitoring electrogram signals, comprising:

implanting in a patient's body a monitoring device comprising an electrogram amplifier, a sensing electrode coupled to the amplifier, storage means for storing electrogram signals, and means for generating an internal electrogram storage trigger signal;

generating an internal electrogram further comprising:
generating an internal electrogram storage trigger signal;
defining a patient trigger confirmation period following the internal electrogram storage trigger signal;
generating a patient trigger signal; and
responsive to receipt of the patient trigger signal within the patient trigger confirmation period, storing electrogram signals.

13. A method according to claim 12, further comprising:

defining an internal trigger confirmation period following the patient trigger signal; and responsive to receipt of an internal electrogram storage trigger signal within the internal trigger confirmation period, storing electrogram signals.

14. A method according to claim 12 or claim 13, further comprising detecting a cardiac arrhythmia and generating the internal electrogram storage trigger signal responsive to detection of the cardiac arrhythmia.

15. A method according to claim 14 wherein generating the patient trigger signal comprises generating a telemetry transmission.

16. A method according to claim 14 wherein generating the patient trigger signal comprises generating a signal detectable by the monitoring device.

17. A method according to claim 12 or claim 13 further comprising detecting a cardiac arrhythmia and generating the internal electrogram storage trigger signal responsive to detection of the cardiac arrhythmia, and detecting termination of an arrhythmia and responsive to the detection of termination of the arrhythmia following generation of an internal electrogram storage trigger signal, prior to receipt of a patient trigger signal, preventing storage of electrogram signals.

* * * * *

UNITED STATES PATENT AND TRADEMARK OFFICE
CERTIFICATE OF CORRECTION

PATENT NO.   : 6,317,626 B1
DATED        : November 13, 2001
INVENTOR(S)  : Eduardo N. Warman It is certified that error appears in the above-identified patent and that said Letters Patent is hereby corrected as shown below:

Column 16,
Line 55, after the word "wherein" insert -- the --.

Signed and Sealed this

Tenth Day of December, 2002

JAMES E. ROGAN
*Director of the United States Patent and Trademark Office*